United States Patent
King et al.

(10) Patent No.: US 11,524,927 B2
(45) Date of Patent: Dec. 13, 2022

(54) SHORT CONTACT, ELEVATED TEMPERATURE MEG RECLAMATION

(71) Applicant: CAMERON INTERNATIONAL CORPORATION, Houston, TX (US)

(72) Inventors: Christopher Stephen King, Houston, TX (US); Brian Edward Messenger, Hook (GB); Harihara V. Nemmara, Katy, TX (US); Z. Frank Zheng, Cypress, TX (US); Shihui Zhou, Middlesex (GB)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 0 days.

(21) Appl. No.: 14/800,876

(22) Filed: Jul. 16, 2015

(65) Prior Publication Data

US 2017/0015613 A1 Jan. 19, 2017

(51) Int. Cl.
*C07C 29/80* (2006.01)
*B01D 3/06* (2006.01)

(52) U.S. Cl.
CPC ............... *C07C 29/80* (2013.01); *B01D 3/06* (2013.01)

(58) Field of Classification Search
CPC .......... C07C 29/80; C07C 31/202; B01D 3/06
See application file for complete search history.

(56) References Cited

U.S. PATENT DOCUMENTS

| 5,993,608 | A | 11/1999 | Abry et al. |
| 6,340,373 | B1 | 1/2002 | Billington |
| 6,444,095 | B1 | 9/2002 | Evans et al. |
| 6,685,802 | B1 | 2/2004 | Nazzer |
| 8,652,304 | B2 | 2/2014 | Nazzer |
| 8,728,321 | B2 | 5/2014 | Nazzer |
| 2008/0081933 | A1* | 4/2008 | Bastings ............... B01D 3/143 568/858 |
| 2008/0283471 | A1 | 11/2008 | Nazzer |
| 2009/0156867 | A1 | 6/2009 | Van Kruchten |

(Continued)

FOREIGN PATENT DOCUMENTS

| WO | 2007073204 A1 | 6/2007 | |
| WO | WO 2007073204 A1 * | 6/2007 | ............. C07C 29/80 |

OTHER PUBLICATIONS

Peppas, N. A. (Ed.). (2012). One Hundred Years of Chemical Engineering: From Lewis M. Norton (MIT 1888) to Present (vol. 9). Springer Science & Business Media.*

(Continued)

*Primary Examiner* — Youngsul Jeong
(74) *Attorney, Agent, or Firm* — Helene Raybaud

(57) ABSTRACT

Monoethylene glycol (MEG) may be reclaimed by a process that includes contacting a MEG-water-salt stream with a heat transfer fluid and then flash separating the MEG and water in the flash separator vessel where the pressure is higher than 0.3 barA (0.03 MPa), the temperature is in the range of above 120° C. to about 250° C., and the residence time of the MEG and water ranges from about 1 second to about 10 minutes, and then removing the MEG and water in an overhead of the flash separator vessel and removing the salt from the flash separator vessel. In some embodiments it is expected that the temperature of the process may range from above 165° C. to about 250° C. and/or that the pressure may be atmospheric.

9 Claims, 1 Drawing Sheet

(56) References Cited

U.S. PATENT DOCUMENTS

2010/0191023 A1 7/2010 Chen et al.
2011/0094871 A1 4/2011 Nazzer
2015/0144477 A1 5/2015 Esquier et al.

OTHER PUBLICATIONS

Zumdahl, S., & DeCoste, D. J. (2012). Chemical principles. Nelson Education.Business Media.*
Int'l Search Report & Written Opinion in PCT/US2016/040309, dated Sep. 8, 2016.
Examination Report issued in the related AU Application 2016292774, dated Jan. 14, 2020 (3 pages).
Office Action Issued in the BR Application 1120180009180, dated Feb. 10, 2020 (8 pages).
Office Action issued in the CN Application 201680041881.9, dated Aug. 14, 2020 (14 pages).
International Preliminary Report on Patentability of International Patent Application No. PCT/US2016/040309, dated Jan. 16, 2018 (5 pages).
Extended Search Report issued in the related EP Application 16824883.9, dated Jan. 25, 2019 (5 pages).
Richardson et al., 2002, Coulson and Richardson's Chemical Engineering vol. 2—Particle Technology Separation Processes (5th Edition), Elsevier (Year: 2002), p. 555.

* cited by examiner

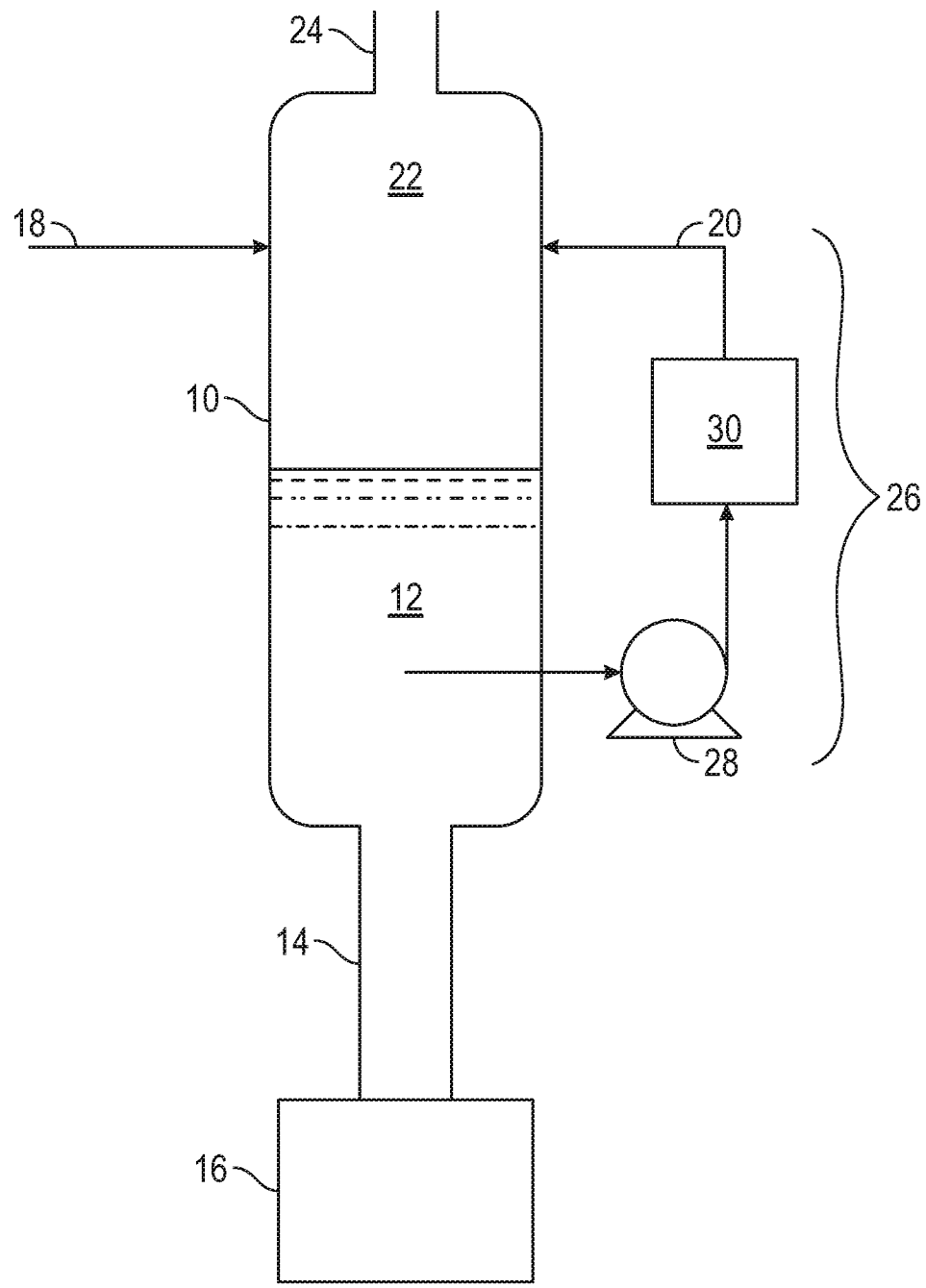

SHORT CONTACT, ELEVATED TEMPERATURE MEG RECLAMATION

BACKGROUND OF THE INVENTION

This invention relates generally to a process for reclaiming monoethylene glycol (MEG) from a water miscible liquid, and more particularly relates to methods for reclaiming MEG with a heat transfer fluid at elevated temperatures and at higher pressures than are conventionally employed.

In conventional MEG reclamation processes, which involve the removal of a salt from a MEG-water solution, a MEG-water-salt stream is contacted with a recycle stream of salt-saturated MEG operating at a temperature above the dew point of the incoming feed such that the volatile components of the feed are fully vaporized and the dissolved salt components of the feed are precipitated and removed from the heat transfer fluid. The recycle MEG stream thus acts as a heat transfer fluid. A hydrocarbon stream (or other non-volatile fluid) may also be employed as the recycle stream.

Conventional MEG reclamation processes include, but are not necessarily limited to, those described in U.S. Pat. No. 6,685,802 ("the '802 patent") the process of U.S. Pat. No. 5,993,608, ("the '608 patent"), the process of U.S. Pat. No. 6,340,373 ("the '373 patent"), the disclosures of which are incorporated in their entirety.

As noted, these processes involve the removal of salt from glycol that is used for dehydrating natural gas and for preventing hydrate formation in oil and gas production facilities. And as mentioned, the demineralization is typically done by a flash vaporization process in which a heated recycle liquid provides heat to vaporise an aqueous stream of glycol while collecting precipitated salt and other solid material in a liquid residue that can then be removed from the process. The processes described in the '802, '608, and '373 patents each include a flash vaporisation process similar to the above and such flash vaporisation processes have been or are being applied in the oil and gas industry to remove unwanted salt from glycol.

The temperature above which MEG degrades significantly is widely accepted to be approximately 165° C. As a result, the flash vaporization process is carried out at sub-atmospheric pressures (0.1-0.3 barA; 0.01-0.03 MPa) in order to achieve complete vaporization of the MEG and water components at temperatures well below the accepted degradation temperature of 165° C. The recycle heater outlet temperature in conventional flash separators is typically limited to an upper value of 150° C. as a consequence of the concern regarding MEG degradation.

Conventional MEG reclamation processes employ a large recirculating inventory of concentrated MEG which is employed to provide the heating duty, as exemplified in U.S. Pat. No. 8,728,321, incorporated herein by reference in its entirety. This recirculating MEG has a very long residence time in the MEG Reclamation system (in the order of several months to several years at the elevated temperatures required for complete vaporization.

The long residence time for the recirculating, salt-saturated, MEG stream (conventionally referred to as recycle MEG) makes the degradation process an issue. As a consequence of this long residence time, operation at reduced pressure has been conventionally deemed essential in order to prevent significant MEG degradation with consequential reduction in pH in the system through degradation of the MEG to formic acid, acetic acid, glycolic acid, and other carboxylic acids. The reduction in pH leads, potentially, to increased corrosion rates. Under such circumstances, in order to maintain an operable system, it is necessary to periodically blowdown and dispose of the degraded MEG from the system resulting in significant MEG losses and potential environmental impact from handling this waste product. Cost of disposal and replacement of MEG can be significant.

It would thus be desirable if an improved process for reclaiming MEG were discovered which minimized or avoided one or more of these problems.

BRIEF SUMMARY OF THE INVENTION

In one non-limiting embodiment there is provided a process to reclaim monoethylene glycol (MEG), where the process includes contacting a stream comprising MEG, water, and at least one salt with a heat transfer fluid, optionally in a flash separator vessel, flash separating the MEG and water from the stream in the flash separator vessel where the pressure is higher than 0.3 barA (0.03 MPa), the temperature is in the range of 110° C. to about 250° C.; alternatively above 150° C. to about 220° C., and the residence time of the MEG and water ranges from about 1 second to about 10 minutes. The process further includes removing the MEG and water in an overhead of the flash separator vessel and removing at least one salt from the flash separator vessel.

BRIEF DESCRIPTION OF DRAWING

FIG. 1 schematically shows a flash separator vessel used in a process for removing solid matter from the lower portion of a vessel that contains process liquid and unwanted solid matter and for removing MEG and water in an overhead.

It will be appreciated that the FIGURE is a schematic illustration that is not to scale or proportion, and, as such, some of the important parts of the invention may be exaggerated for illustration.

DETAILED DESCRIPTION OF THE INVENTION

The method relates to a process where a hydrocarbon stream (or other non-volatile fluid) is employed to provide the heating duty to vaporize the MEG and water components of the feed. It has been discovered that MEG degradation is not instantaneous, and it has been further discovered that a flash separator vessel can be operated at higher pressures without any significant observed increase in MEG degradation products provided that the residence time of the MEG in the flash separator vessel is kept to a minimum. Tests have been carried out at atmospheric pressure, and higher pressure operation in principle should also be achievable.

This finding allows the flash separator vessel to operate at pressures above the currently recognized range of 0.1 to 0.3 barA (0.01 to 0.03 MPa); alternatively where the pressure is atmospheric and above; and in a different non-limiting embodiment where the pressure is from about atmospheric plus 5 psi (1.34 barA), and therefore at temperatures significantly higher than the previously recognized limit of 165° C. The benefits of operating in the range of 0.1 to 0.3 barA (0.01 to 0.03 MPa) include, but are not necessarily limited to:

1) Reduced equipment size due to reduced vapor phase velocity at higher pressure. The flash separator vapors can be discharged to the site flare system without the requirements for a vacuum system.
2) The potential to eliminate the vacuum system which not only saves cost and complexity of the equipment.
3) Reduced potential for oxygen ingress, another cause of MEG degradation.

In more detail, the process involves a MEG/water incoming stream entering a flash separator vessel where the MEG and water vaporizes rapidly and completely at temperatures higher than 150° C. and pressures higher than 0.3 barA (0.03 MPa); alternatively higher than 0.5 barA (0.05 MPa) without any MEG/water inventory remaining in the device which could be exposed to the high temperature for a prolonged period. In one non-limiting embodiment, the temperature of the flash separator is in the range of about or above 110° C., alternatively about or above 120° C. independently to about 250° C.; in another non-limiting embodiment above 150° C. independently to about 220° C.; alternatively from above 165° C. independently to about 220° C. When term "independently" is used herein with respect to a range, it means that any lower threshold may be combined with any upper threshold to give a suitable alternative range. The optimum temperature range is dependent on the composition of the feed input and on the operating pressure. Higher MEG content necessitates higher temperatures. In one non-limiting embodiment, if the liquid pool equilibrium temperature is maintained at about 220° C., but there is a differential temperature across the recycle heat exchanger, and if an elevated temperature is required because the MEG residence time is kept to a minimum, then the recycle heater outlet temperature, and thus the recycle heater differential temperature, may be increased. This may give a further advantage of reducing the recycle flow rate thereby permitting smaller pumps and smaller diameter pipework.

The residence time of the MEG and water ranges from about 1 second independently to about 10 minutes, alternatively from about 10 seconds independently to about 5 minutes, and in a different non-limiting embodiment, from about 20 seconds independently to about 1 minute. In general, the shorter the residence time, the better, but there is a finite amount of time required to warm the feed to its bubble point, and then to vaporize it.

Suitable heat transfer fluids include, but are not necessarily limited to, aromatic hydrocarbons, alcohols, glycols, amines, silicone-based liquids, and mixtures thereof where these heat transfer fluids are not miscible with MEG. In one non-limiting example, a suitable mixture of synthetic aromatic hydrocarbons is THERMINOL® ADX-10 heat transfer fluid available from Solutia Inc. Paraffinic hydrocarbon mixtures such as PARATHERM HE® and XCELTHERM® 600 can also be employed as the heat transfer fluid. Suitable silicone-based liquids include, but are not necessarily limited to, DURATHERM S, and the like.

Salts that may contaminate the feed stream include, but are not necessarily limited to sodium chloride (NaCl), calcium chloride ($CaCl_2$), other chlorides, oxides, sulfates, acetates, nitrates, phosphates, bicarbonates and carbonates of sodium, potassium, calcium, magnesium, iron, copper, lead, barium, strontium, and the like, and combinations thereof. In addition, the feed stream may also contain a number of optional flow assurance chemicals such as scale inhibitors, corrosion inhibitors, wax inhibitors and oxygen scavengers As shown in FIG. 1, the lower portion of a flash separator vessel 10 contains a mixture including process liquid 12 (i.e. the heat transfer fluid) that is substantially immiscible with water and undissolved solid matter or salt in particulate form. The undissolved solids may be removed from the process by a variety of technologies including, but not necessarily limited to, a conveying means such as a downcomer pipe 14 which is connected proximate the base of the vessel 10 to a solids collection tank 16. Removal of the solids from the process may be achieved employing one of a variety of commercially available solids-liquids separation processes such as settling tanks (as shown in FIG. 1) or centrifuges. The feed stream 18 is a free flowing mixture including two or more miscible liquids (e.g. MEG and water) and dissolved solids (e.g. sodium chloride, magnesium chloride, calcium chloride from the gas production well and flow assurance chemicals added to the MEG-water solution to minimize pipescaling and pipeline corrosion). Examples of such mixtures include glycol/water and amine/water that are contaminated with dissolved salts, corrosion products and/or other unwanted solids.

The present process may be termed a "Flash-on-Oil" process (FoA). It is true that for FoO as well as for conventional MEG processes that one or more of the liquid component(s) boils at a significantly higher temperature than the other liquid components, but the present FoO process is operated such that, regardless of the differing boiling points, both (or all) of the components of the feed are fully vaporized. This is not the case in the conventional system where there is equilibrium between the incoming MEG-water and the Recycle MEG such that a substantial inventory of MEG remains within the vessel. If the FoO process is properly optimized, then the quantity of MEG (water) present in the liquid phase in the vessel will be small.

The feed stream 18 enters the flash separator vessel 10 and mixes with a larger and hotter stream of recycle liquor 20 that has also entered the separation vessel 10. The recycle liquor 20 in one non-limiting embodiment immediately heats the feed stream 18 and thereby causes the volatile components in the feed stream 18 to boil rapidly or flash.

Alternatively, the feed stream 18 and recycle liquor 20 may be mixed upstream (not shown) of the separator vessel 10 and the commingled streams injected into the separation vessel 10.

The vapor 22 generated by the flashing feed stream flows out of the separation vessel through the outlet channel 24. This vapor contains essentially no solids unless there is significant carryover of small particles or liquid droplets into the vapour. In one non-limiting embodiment the vapor is MEG and water.

Solids and unvaporised liquid collect in liquid pool 12 in the lower half of the separation vessel 10. The flash vaporisation that has occurred ensures that the liquid pool is composed mainly of the higher boiling point liquid (i.e. the heat transfer fluid) and solids. A recycle liquor 20, is drawn from the liquid pool and enters the recycle circuit 26 where it is pumped by the recycle pump 28, heated by the recycle heater 30 and mixed with the feed stream 18 as described above. An objective of the process herein is to minimize or prevent any MEG accumulation in the loop. This may be achieved by operating at a suitable temperature-pressure-residence time.

The method employs short residence time for the MEG molecules in the Flash Vaporization zone in order to minimize thermal and oxidative-thermal degradation of the MEG molecules to organic acids and other species. Employing short residence times allows operating pressures at or close to ambient (atmospheric) to be employed. The temperature-pressure regime employed in the method is such that complete vaporization of the MEG and water components of the incoming feed stream is achieved.

There are significant and substantial benefits in operating at pressures close to atmospheric pressure rather than the 0.1-0.3 barA (0.01-0.03 MPa) conventionally employed for the flash vaporization process. These are exemplified below:

1) Degradation of MEG and Corrosion: In conventional MEG reclamation methods operated under partial vacuum, there is increased potential for ingress of air into the flash separator vessel through leakage at the flanges and fittings. The oxygen present in the incoming air can result in increased degradation of the MEG to organic acids which in turn can result in increased corrosion of pipework. Operating at atmospheric pressure or above will significantly reduce potential for air ingress. In one non-limiting embodiment the flash separator vessel will be operated at a pressure slightly above atmospheric pressure. In another non-restrictive version the actual operating pressure will be determined by equipment and pipework downstream of the vessel, but the operating pressure may likely be around 5 psiG (20 psiA, 1.35 bar A).

2) Complex Vacuum System: Operation at the reduced pressure of conventional MEG reclamation methods requires a vacuum system. The vacuum system can be complex and adds additional weight, space requirements and utility (electrical and cooling medium) demand on the MEG package. Space and weight restrictions are important particularly for off-shore applications where space and weight are at a premium. Operation of the Flash Separator at atmospheric pressure as in the present method would remove the requirement for a vacuum package.

3) Large Diameter Vessels and Pipework: Operation at low pressure (0.1-0.3 barA (0.01-0.03 MPa)) results in the production of large volumes of low density vapor (MEG-water) from the flash vaporization process. This large volumetric flow requires a large flash separator vessel, large diameter pipework and larger equipment (typically condenser, knockout drum and distillation column) downstream of the Flash Separator vessel. In the present method, operating at atmospheric pressure will reduce the size of the Flash Separator vessel, pipework and downstream equipment treating the overhead vapors. Size (surface area) of condenser equipment in the Reclaimer section will also be reduced by operating at atmospheric pressure.

In the foregoing specification, the disclosure has been described with reference to specific embodiments thereof, and is expected to be effective in providing methods and apparatus that improve the reclamation of MEG by allowing the flash separator to operate at pressures above the currently recognized range, even at atmospheric pressure, and therefore, at temperatures significantly higher than the conventionally recognized limit of 165° C. However, it will be evident that various modifications and changes may be made thereto without departing from the broader scope of the disclosure as set forth in the appended claims. Accordingly, the specification is to be regarded in an illustrative rather than a restrictive sense. For example, the MEG-water-salt composition, heat transfer fluids, pressures, temperatures, residence times, and/or flow rates may be changed or optimized from that illustrated and described, and even though certain additional features are not specifically identified or tried in a particular system, method or apparatus described herein, they would be anticipated to be within the scope of this disclosure. For instance, the parameters, compositions and treatments any of the described components and equipment would be expected to find utility and be encompassed by the appended claims.

The words "comprising" and "comprises" as used throughout the claims are to be interpreted as "including but not limited to".

The present disclosure may suitably comprise, consist or consist essentially of the elements disclosed and may be practiced in the absence of an element not disclosed. For instance, in one non-limiting embodiment, there may be provided a process to reclaim monoethylene glycol (MEG), the process consisting essentially of, or consisting of, contacting a stream comprising MEG, water, and at least one salt with a heat transfer fluid, optionally in a flash separator vessel; flash separating the MEG and water from the stream in the flash separator vessel where: the pressure is higher than 0.3 barA (0.03 MPa); the temperature is in the range of about 110° C. to about 250° C.; and the residence time of the MEG and water ranges from about 1 second to about 10 minutes. The process may further consist essentially of, or consist of, removing the MEG and water in an overhead of the flash separator vessel and removing the at least one salt from the flash separator vessel.

What is claimed is:

1. A process to reclaim monoethylene glycol (MEG), the process comprising:
    using a heated transfer fluid to directly contact a stream comprising MEG, water, and at least one salt in a flash separator vessel, wherein the heated transfer fluid is immiscible with MEG;
    flashing the MEG and water by the thermal direct contact with the heated transfer fluid in the flash separator vessel;
    removing the MEG and water in an overhead of the flash separator vessel; and
    removing the at least one salt from the flash separator vessel.

2. The process of claim 1, wherein the flashing the MEG and water is conducted at a temperature of about 110° C. to about 250° C.

3. The process of claim 1, wherein the heated transfer fluid is selected from the group consisting of aromatic hydrocarbons, paraffinic hydrocarbons, silicone-based liquids and mixtures thereof.

4. The method of claim 1, wherein a volume of the heated transfer fluid is greater than a volume of the stream comprising MEG, water, and at least one salt.

5. A process to reclaim monoethylene glycol (MEG), the process comprising:
    using a hydrocarbon heated transfer fluid to directly contact a stream comprising MEG, water, and at least one salt in a flash separator vessel, wherein the hydrocarbon heated transfer fluid is immiscible with MEG;
    flashing the MEG and water by the thermal contact with the hydrocarbon heated transfer fluid at a pressure higher than 0.5 barA in the flash separator vessel;
    removing the MEG and water in an overhead of the flash separator vessel; and
    removing the at least one salt from the flash separator vessel.

6. The method of claim 5, wherein a volume of the hydrocarbon heated transfer fluid is greater than a volume of the stream comprising MEG, water, and at least one salt.

7. A process to reclaim monoethylene glycol (MEG), the process comprising:

using a heated transfer fluid to directly contact a stream comprising MEG, water, and at least one salt in a flash separator vessel, wherein the heated transfer fluid is immiscible with MEG;

completely flashing the MEG and water in the heated transfer fluid with a residence time of about 1 second to about 10 minutes;

removing the MEG and water in an overhead of the flash separator vessel; and removing the at least one salt from the flash separator vessel.

8. The process of claim 7, wherein the heated transfer fluid is selected from the group consisting of aromatic hydrocarbons, paraffinic hydrocarbons, silicone-based liquids and mixtures thereof.

9. The method of claim 7, wherein a volume of the heated transfer fluid is greater than a volume of the stream comprising MEG, water, and at least one salt.

* * * * *